(12) United States Patent
Lemelson

(10) Patent No.: US 6,491,663 B1
(45) Date of Patent: Dec. 10, 2002

(54) MEDICAL DEVICES USING ELECTROSENSITIVE GELS

(76) Inventor: Jerome H. Lemelson, Suite 286, 930 Tahoe Blvd. Unit 802, Incline Village, NV (US) 89451-9436

( * ) Notice: Subject to any disclaimer, the term of this patent is extended or adjusted under 35 U.S.C. 154(b) by 0 days.

(21) Appl. No.: 09/544,100

(22) Filed: Apr. 6, 2000

Related U.S. Application Data

(62) Division of application No. 09/039,667, filed on Mar. 16, 1998, now Pat. No. 6,090,139, which is a division of application No. 08/662,345, filed on Jun. 12, 1996, now Pat. No. 5,800,421.

(51) Int. Cl.[7] .................. A61M 31/00; A61M 37/00
(52) U.S. Cl. ................... 604/103.02; 604/916
(58) Field of Search ............ 604/4, 890.1, 891.1, 604/131, 132, 153, 246, 524, 523, 525, 96.01, 164.03, 916, 103.01–103.02; 222/95, 96; 138/137

(56) References Cited

U.S. PATENT DOCUMENTS

| | | | |
|---|---|---|---|
| 5,800,421 A | * 9/1998 | Lemelson | 222/95 |
| 5,951,600 A | * 9/1999 | Lemelson | 623/2.1 |
| 6,090,139 A | * 7/2000 | Lemelson | 623/2.1 |
| 6,096,023 A | * 8/2000 | Lemelson | 604/524 |
| 6,287,294 B1 | * 9/2001 | Lemelson | 604/132 |

\* cited by examiner

*Primary Examiner*—Anhtuan T. Nguyen
*Assistant Examiner*—Michael M Thompson
(74) *Attorney, Agent, or Firm*—Niro, Scavone Haller & Niro

(57) ABSTRACT

A balloon catheter having an elongated tubular portion having a proximal end portion and a distal end portion. The balloon is attached to the catheter near the distal end portion. At least one reservoir is attached to the balloon. An expandable copolymer gel fills the reservoir and an electrode is operably attached to the expandable copolymer gel. This permits the balloon to change shape in response to a voltage applied to the electrode.

2 Claims, 5 Drawing Sheets

MEDICAL DEVICES USING ELECTROSENSITIVE GELS

This application is Division of Ser. No. 09/039,667 filed Mar. 16, 1998 U.S. Pat No. 6,090,139 which; is a division of 08/662,345 filed Jun. 12, 1996 U.S. Pat. No. 5,800,421.

FIELD OF THE INVENTION

This invention relates to medical devices, including drug delivery systems, catheters, and heart valves, that use electrosensitive gels ("electro-gels") to provide real time electrical control of the motion and/or physical properties of key portions of the devices. Computer control methods for optimizing the performance of such devices are also disclosed and claimed.

BACKGROUND OF THE INVENTION

Two basic types of electrosensitive gel materials exist. The first type includes certain gelled copolymers which, when placed in aqueous solution, undergo reversible contraction or expansion in response to very small changes in pH. Typically, the pH changes are induced by the application of electrical potential differences to the solution, thus producing an electrically controllable response. The response actually takes the form of a change in volume of the expandable copolymer resulting from uptake of the solution at high pH levels, or release of the solution at low pH levels. Thus, the response is said to be linear and homogenous in the sense that, for example, a long cylindrical piece of gel would undergo the same amount of relative percentage change in length and diameter. Percentage changes of more than 400% have been observed. Expandable copolymer gels of this type are described in U.S. Pat. No. 5,100,933 (Tanaka, et al); in U.S. Pat. No. 5,250,167 (Adolf, et al); and in U.S. Pat. No. 5,389,222 (Shahinpoor, et al), the disclosures of which are incorporated by reference herein.

Expandable copolymer gels of these types may comprise three dimensional networks consisting of polyacrylic acid that can be obtained by heating a foil of polyacrylic acid containing a polyvalent alcohol such as glycerol or polyvinyl alcohol. The resulting three dimensional network is insoluble in water, but swells in response to high pH and contracts in response to low pH. Electric fields in the range of a few volts per centimeter suffice to stimulate that response.

Thus, for example, U.S. Pat. No. 5,250,167 (Adolf, et al) discloses a variety of mechanisms based on encapsulated polyelectrolyte polymeric gels in aqueous electrolytic solutions, which undergo reversible expansion and contraction in response to electric fields in the range of a few volts per centimeter as a result of changing the pH of the solution. Adolf discloses that filaments of copolymer gel may be proposed for most applications. The specific machines he describes and depicts in FIGS. 1 through 6 are quite simple and are constrained by the need to immerse the copolymer fibers in an aqueous electrolyte solution, which must not be allowed to leak away. Fundamentally, his machines rely upon simple linear contraction. A critical point is that, while both an anode and a cathode are required, the fibers ordinarily should be connected to only one of the two electrodes, leaving a gap 26 shown in FIGS.1 and 2. According to Adolf, if the gap is omitted and opposite ends of the copolymer gel fibers are connected to electrodes of opposite polarity, the result would be expansion near one electrode and contraction near the other, with little or no net change in length.

Fundamentally, Adolf discloses only simple push-pull mechanisms (FIGS. 1–2), bending mechanisms (FIGS. 3–4), and an oscillator (FIG. 6). (Adolf's FIG. 5 is a push-pull mechanism in which the electrodes that change pH of the solution are physically separated from the copolymer gel; the gel responds to pumping of high or low pH solution into its container.)

Other investigators have suggested bendable structures as shown in FIG. 3 of U.S. Pat. No. 5,389,222 (Shahinpoor, et al), in which one side of a sheet of expandable copolymer gel is made to expand, while the other side is made to contract in response to an electrical field applied across the section of the sheet. (This, of course, takes advantage of the effect of eliminating the gap mentioned in FIGS. 1–2 of the Adolf '167 patent). Shahinpoor also discloses a sphincter-like device (FIG. 4) which closes in response to the application of an electrical field. He also mentions a spring-loaded device (FIG. 5) in which an oscillating rotary motion is produced by contraction of a gel element.

The second type of electrosensitive gel involves both a different electrochemical mechanism and different mechanical results. Such gels are variously termed electrorheological gels or ER gels or fluids, that exhibit a phenomenon called the Winslow effect. These ER gel or fluid materials typically comprise a dielectric fluid in which is dispersed a plurality of microscopic electrorheologically sensitive particles. Application of an electrical field to such a composite material alters the pattern of electrical charge distribution on the surface of the electrorheological particles, causing them to be attracted to each other and to become aligned in a regular fashion, effectively forming chains of microscopic fibers between the electrodes. The electrorheological particles may include silica, starch, carboxy-modified polyacrylamides, and similar materials which will function only in the presence of some water. Other materials such as organic semiconductors, including silicone ionomers, are said to be capable of functioning without water. See, for example, U.S. Pat. No. 4,772,407 (Carlson); U.S. Pat. No. 5,032,307 (Carlson); U.S. Pat. No. 5,252,249 (Kurachi, et al); U.S. Pat. No. 5,252,250 (Endo, et al) ; and U.S. Pat. No. 5,412,006 (Fisher, et al), the disclosures of which are incorporated by reference herein.

In either case, the salient characteristic of ER gels is that the application of a voltage difference results in a macroscopic change from liquid-like behavior to essentially solid behavior. That is, the ER fluids or gels change from behaving as Newtonian fluids, which deform continuously and without limit in response to the application of any stress (force) at all, to Bingham plastic fluids, which will not deform at all until some threshold level of yield stress (force) is applied. The storage modulus G' and the loss modulus G" also change dramatically in response to application of voltage gradients to these materials. (These moduli relate to the ability of the material to damp energy.) Electrical current flows are said to be low, and response times are of the order of milliseconds.

ER gels are used in automotive transmissions, clutches, vibration dampeners, and brakes. One investigator suggests using such gels as base materials for the ink used in ink jet printers. See U.S. Pat. No. 5,326,489 (Asako, et al). In addition, U.S. Pat. No. 5,213,713 (Reitz) proposes a variety of simple shapes comprising various beams, angles, and the like which include one or more portions made of ER gel. By temporarily applying an electrical potential to the electrorheological solid portion of such items, their shape can be changed by mechanically bending the item and then removing the electrical field, whereupon the electrorheological solid portion "freezes" into the new shape. Notably, however, most ER gels exhibit behavior opposite to that described by Reitz: that is, usually the application of an electrical field to an ER fluid or gel results in solidification, not liquefaction.

Among the drawbacks of the prior art in the area of expandable copolymer gels are the comparatively slow response times and the need for immersion in water. And although ER gels have rapid response times, they are not suited for direct creation of motion.

SUMMARY OF THE INVENTION

My invention provides a group of novel medical devices utilizing the special properties of expandable copolymer gels and ER gels in order to perform such functions as controlled drug delivery; vascular access; arterial plaque removal; and control of blood flow in the heart. In appropriate situations, real time computer control can be used to optimize performance of such devices. Imaging techniques using x-radiation or other forms of imaging energy can be used as sensors to assist in the control of such devices.

Accordingly, it is an object of this invention to provide a variety of approved medical devices.

It is another object of this invention to provide certain medical devices that can advantageously be controlled in real time using computer imaging technology.

It is a further object of this invention to provide machines using expandable copolymer gels that exhibit dramatically improved response times compared to prior art devices.

These and other features, objects and advantages of my invention will be apparent upon consideration of the following detailed description of the invention.

DETAILED DESCRIPTION OF THE PREFERRED EMBODIMENTS

Figure 1:
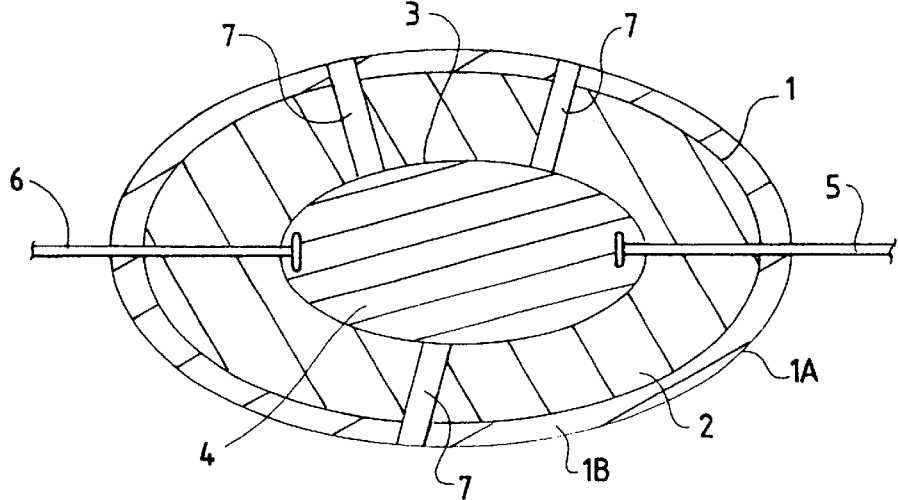
FIG. 1 shows a drug delivery system in which an aliquot of drug is contained within a permeable membrane, along with an expandable copolymer gel.

Referring now to FIG. 1, a simple drug delivery system powered by expandable copolymer gel comprises a permeable membrane 1 which encloses a layer of expandable copolymer gel 2. Inside the layer of expandable copolymer gel is a thin, flexible sack 3 which contains a dose of a drug 4. (The term "drug" is used herein to include any medicine, narcotic, biologically active material, or fluid that may be injected into a body.) First electrode means 5 attached to the expandable copolymer gel 2 is used to supply the voltage required for actuation. Second electrode means 6 may be positioned in convenient proximity within the body to provide the other half of the actuating circuit.

The device is fabricated in a sterile aqueous environment, to maintain the gel in its swelled state. A membrane permeable to water is used to enclose the gel, and to provide the continuous contact with water which is required for operation. The device must be kept in water until used. At a desired time after the device has been positioned at an appropriate location within the body, for example, in a blood vessel or other body duct, the drug is discharged from the device as follows. An electrical potential in the neighborhood of two to three volts is applied between the first and second electrode means for a sufficient time to induce rupture of the sack 3. As the expandable copolymer gel continues to contract, the drug 4 escapes from the ruptured sack and is forced out into the body through the permeable membrane. In the preferred embodiment shown in FIG. 1, the expandable copolymer gel is transpierced by one or more passages 7 which provide a direct pathway for the drug to the exterior of the permeable membrane, thus preventing mixing of the drug with the expandable copolymer gel. Optionally, the permeable membrane surrounding the expandable copolymer gel may itself be enclosed within an impermeable, flexible container 1A, which encloses not only the permeable membrane 1 and the gel 2, but also a sealed electrolyte solution 1B in which the gel can operate without exchanging liquid with the surrounding body fluids.

In a further embodiment, the applied voltage is controlled based on a predetermined dosage versus time regime. That is, since a particular voltage corresponds to a known amount of contraction, calibrated amounts of the initial aliquot of drug are expelled as a particular voltage level is reached. By gradually increasing the voltage, any desired dose versus time response can be obtained.

In still another embodiment of the invention, one or more biological parameters (for example, blood pressure, blood sugar level, blood oxygen content, concentration of drug in the blood stream, etc.) are continuously monitored during operation of the drug delivery device. Feedback control is used to regulate the amount of drug delivered, so as to hold the measured biological parameter within predetermined limits.

Figure 2:
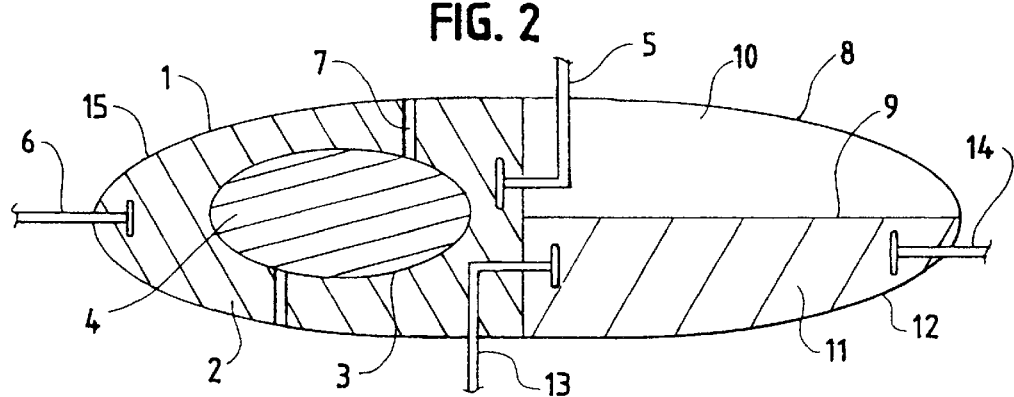
FIG. 2 shows a self-propelled drug delivery system in which an expandable copolymer gel actuates a swimming motion in response to pulsed applications of an electrical field.

The embodiment of FIG. 2 is a self-propelled drug delivery system which makes use of the expansion and contraction of expandable copolymer gels to move an aliquot of drug through a blood vessel or other body duct to a specific location before delivery of the drug. The device comprises a propulsion container 8 divided into at least two compartments by a flexible septum 9. The container 8 may preferably be of generally cylindrical shape, as shown in the figure. First compartment 10 of the propulsion container may be filled with a flexible, inert material such as a non-electrosensitive silicone gel. Second compartment 11 of the propulsion container is enclosed by permeable membrane 12 and is filled with an expandable copolymer gel. The alternate application and removal of an electric potential between first propulsion electrode means 13 and second propulsion electrode means 14 results in cyclic expansion and contraction of the expandable copolymer, which causes flexing of the propulsion container 8. The result is that propulsion container 8 "swims" through the body duct like a snake, until a desired location has been reached. Advantageously, a radio opaque substance may be included in second compartment 11, to enable observation of the location of the device during operation, and control of its position.

When the device has reached the desired location (or at any time during its journey to that location), a drug delivery container 15 is operated to deliver the drug. The structure and operation of drug delivery container 15 is substantially as described above, in connection with the device shown in FIG. 1.

Figure 3:
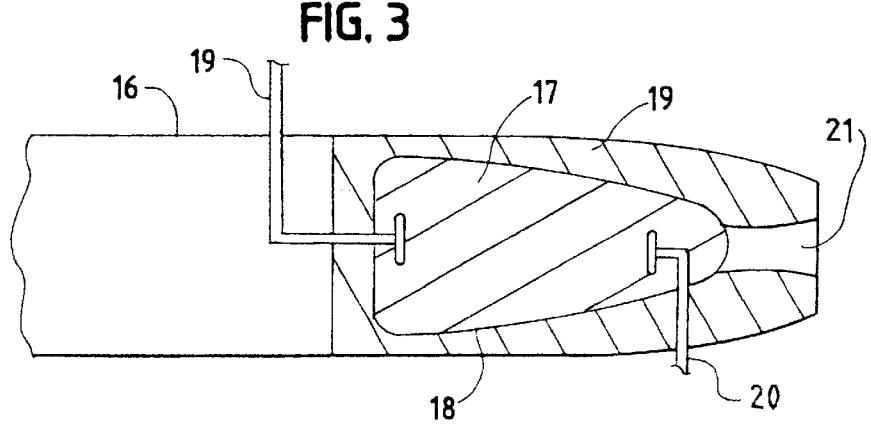
FIG. 3 illustrates a catheter tip in which an expandable copolymer gel is used to expel a measured aliquot of drug.

Referring now to FIG. 3, a catheter tip 16 is shown containing a reservoir 17 of drug or other biologically active material. The drug is contained within a sack 18, which in turn is surrounded by a ring or annulus 19 of expandable copolymer. When the catheter tip has been advanced to the desired location within a blood vessel or other body duct, a voltage is applied between first electrode means 19 and second electrode means 20, causing the expandable copolymer to contract and expelling the drug through one or more orifices 21 at the tip of the catheter. Again, the feedback computer control techniques mentioned above can be used to control the rate and quantity of drug delivery.

A common difficulty encountered in the use of in-dwelling catheters which must remain in the body for weeks or months at a time is abrasion of blood vessel walls and resulting infection, lysis of blood cells, and clot formation. Hard, rigid catheter walls contribute substantially to these problems.

Rigid wall and tip portions of catheters are desirable, however, during implantation procedures. For example, acute hemodialysis catheters are often fabricated of plastic materials which are sufficiently stiff to enable percutaneous insertion without the requirement of making a surgical cutdown to the vein. Such rigidity and stiffness makes implantation much simpler, but becomes a liability after implantation.

Figure 4:
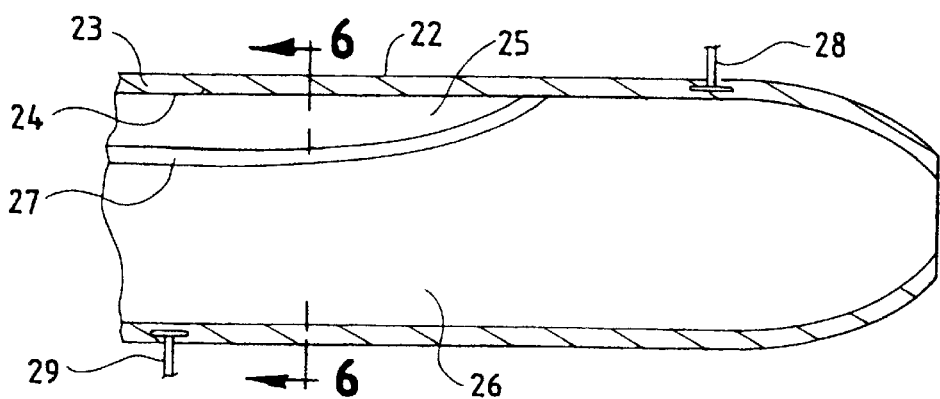
FIG. 4 shows a catheter having variable rigidity, based on incorporation of an ER gel.

FIG. 4 shows a catheter that is especially suitable for hemodialysis, chronic drug infusion or other long-term use in which the catheter remains in the body for a long period of time after implantation. The stiffness of the catheter is electrically controlled using an ER gel, allowing it to be very stiff when implanted and very flexible thereafter. Referring to the cross-sectional drawing of FIG. 6, the catheter uses an elongated, hollow wall filled with ER gel. In the specific embodiment shown, outer wall 22 of the catheter encloses a comparatively thin annular layer 23 of ER gel, sandwiched between outer wall 22 and inner wall 24. The interior of the catheter may include one or more lumens 25, 26 which may be separated from each other by a flat septum 27, as would be the case for the chronic hemodialysis catheters. It will be understood that the catheter shown and described is applicable not only to chronic hemodialysis but also to other operations involving insertion of catheters into cavities in the body.

Figure 5:
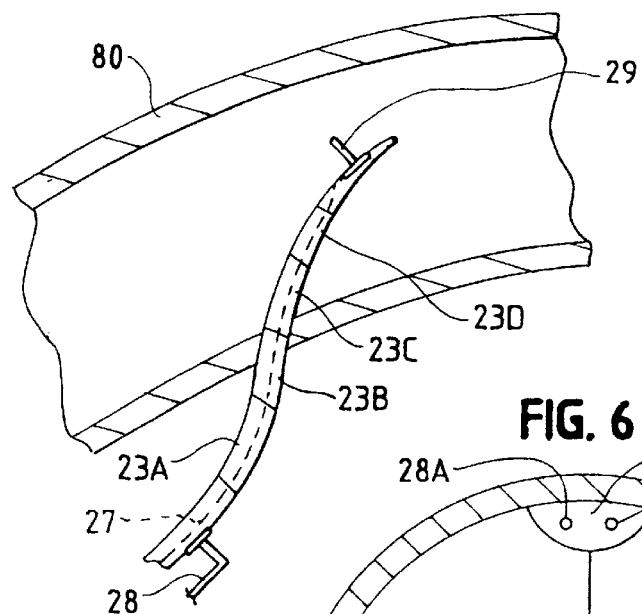
FIG. 5 shows another view of a catheter having variable rigidity, independently controllable at various portions along its length.
Figure 6:
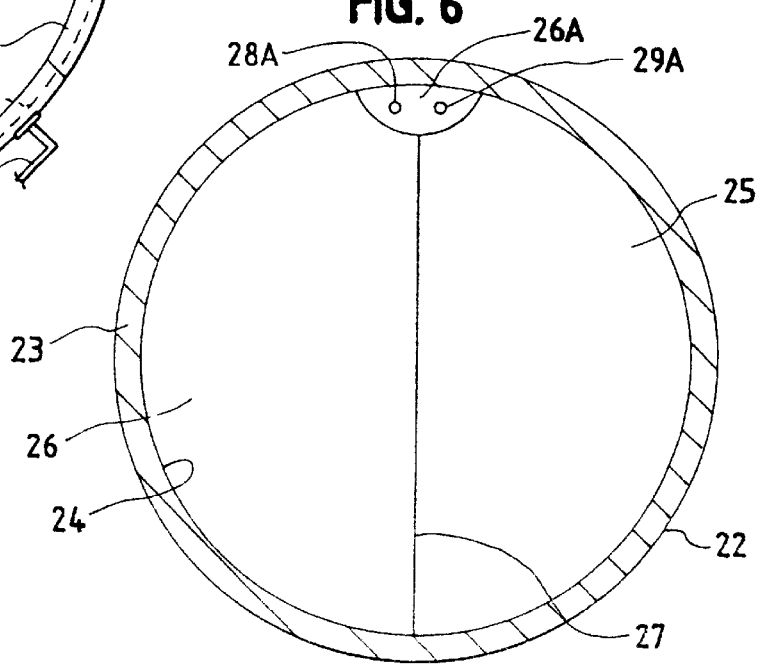
FIG. 6 shows a cross-section of the catheter of FIG. 4.

The overall configuration of the catheter employing this invention appears in FIG. 5. During implantation of the catheter, an electrical potential is applied between first electrode means 28 and second electrode means 29, causing the ER gel in the annulus to become rigid. This facilitates percutaneous insertion of the catheter, without need for surgical cutdown to the blood vessel 80. The rigidity of the catheter can be controlled during implantation by varying the applied voltage, ensuring that a desired level of rigidity is maintained throughout the implantation procedure. Optionally, a plurality of separate sections or reservoirs 23A, 23B, etc. of ER gel along the length of the catheter may be used, as shown is FIG. 5, with separate pairs of electrode means associated with each reservoir. The wiring 28A, 29A associated with the electrode means may be embedded as foil in the catheter wall, or may be run through an extra lumen 26A near the interior wall, as shown in FIG. 6. By this means, the rigidity of various portions of the catheter can be independently controlled by varying the voltage applied to specific sections of the catheter as desired. Preferably, the catheter wall may be fabricated comprising sufficient radio opaque material to enable x-ray observation of its position.

In either embodiment, once the catheter has been implanted and properly positioned, the electrical potential is removed, and the ER gel thereupon becomes liquid. This reduces the rigidity of the catheter to only such stiffness as is provided by the catheter walls themselves. For applications such as chronic hemodialysis, silicone catheter walls are preferable, but other suitable materials, as known to those skilled in the art, may be employed as desired.

Another common difficulty encountered with both chronic and acute vascular access devices such as hemodialysis catheters is formation of clots. Thrombogenesis may occur as a result of flow stagnation in dead spaces within the catheter or as a result of lysis of blood cells induced by excessive levels of shear in the blood flow pattern. In addition, clotting may occur at inlet or outlet apertures, especially if an inlet aperture has been blocked or occluded by contact with the vessel wall, thereby restricting or stopping the blood flow altogether.

Figure 7:
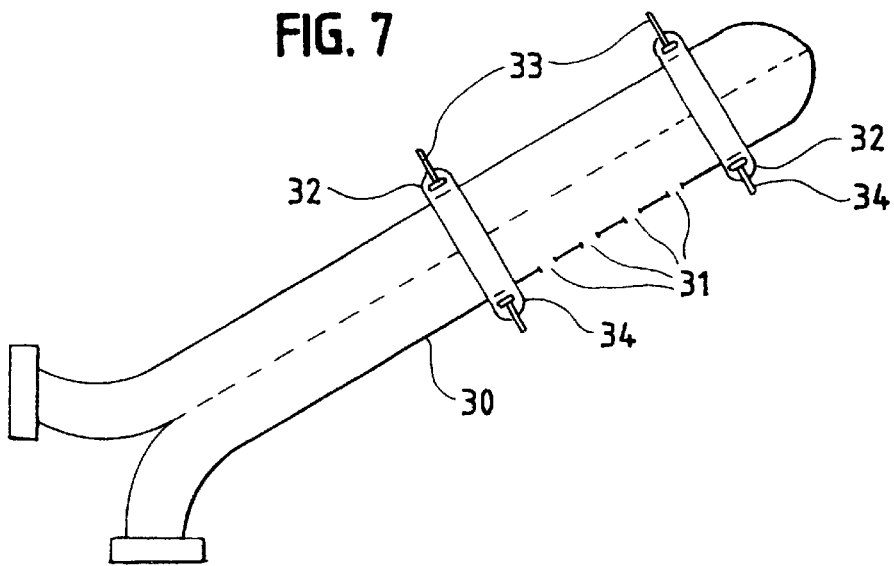
FIG. 7 shows a catheter fitted with devices for prevention of occlusion of intake holes.

Referring now to FIG. 7, a hemodialysis-type catheter is shown that utilizes expandable copolymer gel to discourage clot formation and to help dislodge clots which may form during operation. The embodiment of FIG. 7 also shows a mechanism for preventing occlusion of intake holes by blood vessel walls. The exterior wall 30 of the catheter tube features a plurality of holes 31, which serves as intake holes leading into the withdrawal lumen of the catheter. On either side of the plurality of intake holes 31, there is a toroidal reservoir 32 filled with expandable copolymer gel and fitted with electrode means 33 and 34. In the event that clotting occurs at the intake holes, or blood flow decreases or stops as a result of occlusion of the intake holes by resting against the vessel wall, an electrical potential is applied to the toroidal reservoirs of expandable copolymer gel, causing them to swell and expand, thus pulling the intake holes away from the vessel wall and also dislodging any blood clots that may have begun to form. When normal operation has been restored, the voltage may be removed, leaving a highly flexible catheter in place.

In another version of this embodiment, a plurality of toroidal reservoirs of expandable copolymer gel may be provided along the length of the catheter or may be embedded at intervals within the exterior wall of the catheter. Sequential activation of these reservoirs of expandable copolymer gel results in peristaltic contraction of the wall of the catheter. This not only facilitates dislodging any blood clots which may have formed, it can also help to pump blood or other fluid, such as a viscous drug, through one or more lumens of the catheter. It would be apparent to those of ordinary skill, of course, that various arrangements of reservoirs of expandable copolymer gel can be used, depending on the type of peristaltic motion which it is desired to create in the catheter.

Figure 8:
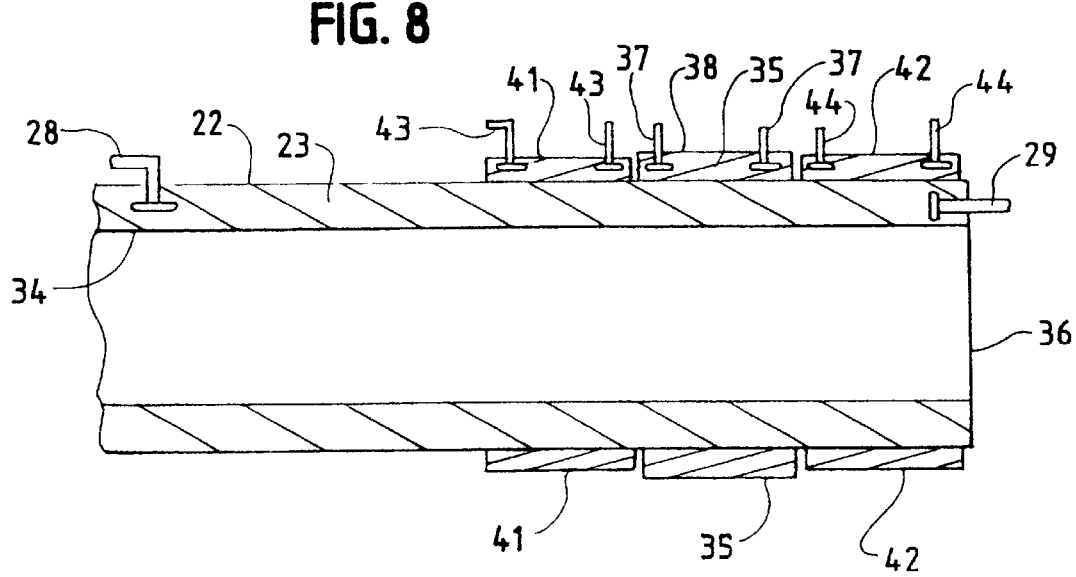
FIG. 8 illustrates an endoscopic device for removal of plaque from blood vessels utilizing an expandable copolymer gel drive mechanism.

Referring now to FIG. 8, there is shown an endoscopic device for the removal of plaque from the walls of a blood vessel. An operation currently performed using complex mechanical devices which must be threaded through vessels approaching the heart before operation. In my invention, a catheter having walls of variable rigidity which are achieved using the system of FIGS. 4 through 6 are first advanced to the location within a major vessel from which plaque deposits are to be removed. When that location is reached, the ER gel within reservoir 35 near the working end 36 of the catheter is energized by electrode means 37, to create a stiff, abrasive portion near the distal end of the catheter. The abrasive portion is equipped with one or more outward-facing walls 38 having a highly abrasive texture. At the proximal end of the abrasive portion of the catheter, there is a proximal reservoir 41 filled with expandable copolymer gel, which is attached to the abrasive portion. That reservoir, in turn, is fitted with paired electrode means 43, which enable alternate expansion and contraction of the reservoir. There is a corresponding distal reservoir 42 attached to the distal end of the abrasive portion, and having paired electrode means 44. Cyclic actuation of the proximal reservoir 41 and the distal reservoir 42 by alternating application of voltage to electrode means 43 and 44 produces a back and forth grinding motion of the abrasive, stiff section 37. This results in abrasion of plaque off of the vessel walls.

Optionally, radio opaque materials may be used in the abrasive portion to assist in visualization of the plaque removal operation using an x-ray.

A class of catheters known generally as "balloon catheters" is used for a variety of purposes within the body. In addition to plaque removal by expansion within a blood vessel, balloon catheters also may be used to restrict or stop blood flow at various locations to enable different types of surgical procedures to be conducted; to divert blood flow or to facilitate the injection of drugs to desired locations.

Figure 9:
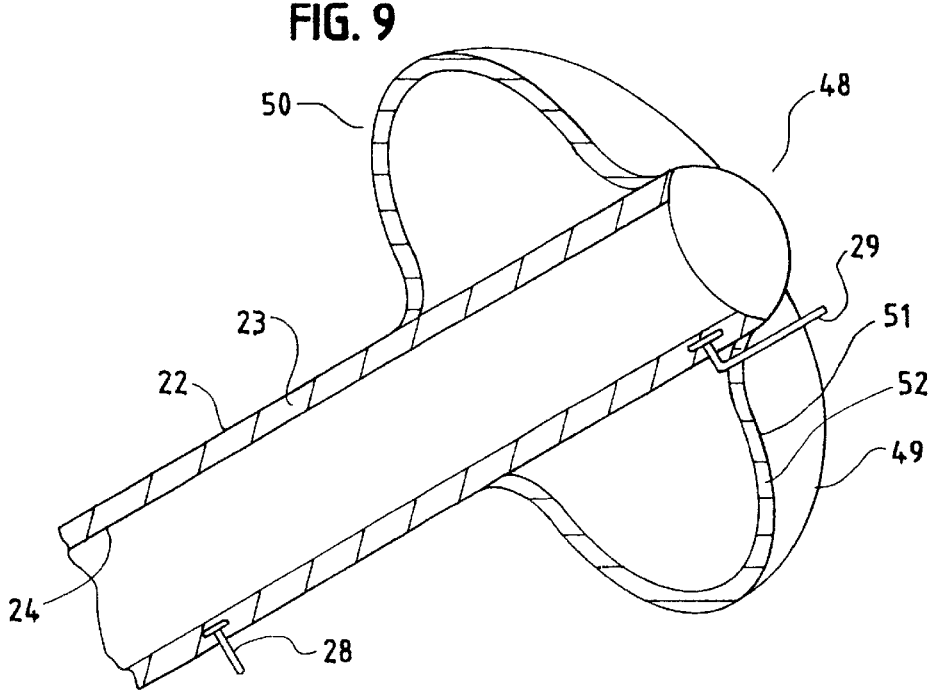
FIG. 9 illustrates a balloon catheter having a shape controlled by expandable copolymer gel, based on dynamic measurements of circulatory system parameters.

FIG. 9 shows a balloon catheter 48 having a generally elongated shape in which the flexible wall 49 of the balloon 50 is stiffened with ribs 51 that comprise reservoirs 52 containing expandable copolymer gel. The size of the balloon 50 may be expanded or contracted, and its shape may be altered by selective application of electrical potentials to one or more of the expandable copolymer gel-filled reservoirs. Optionally, radio opaque material may be incorporated into select locations in the wall of the balloon to facilitate x-ray visualization of its shape. Images formed thereby may be used to control the action of the balloon based on real time calculations matching the desired size and/or shape history. Alternatively, or in addition, one or more biological parameters such as blood pressure, blood flow rate, or other measured variables may be used as control points for altering the shape or size of the balloon.

It is often necessary to place defective heart valves with various types of prosthetic devices. Among those devices are ball-and-cage valves which are sewn onto the heart muscle; and heart valves grafted from pigs. The former types of mechanical devices have been subject to failures associated with defective welds and similar quality control problems, whereas heart valves transplanted from animals may pose rejection problems.

Figure 10:
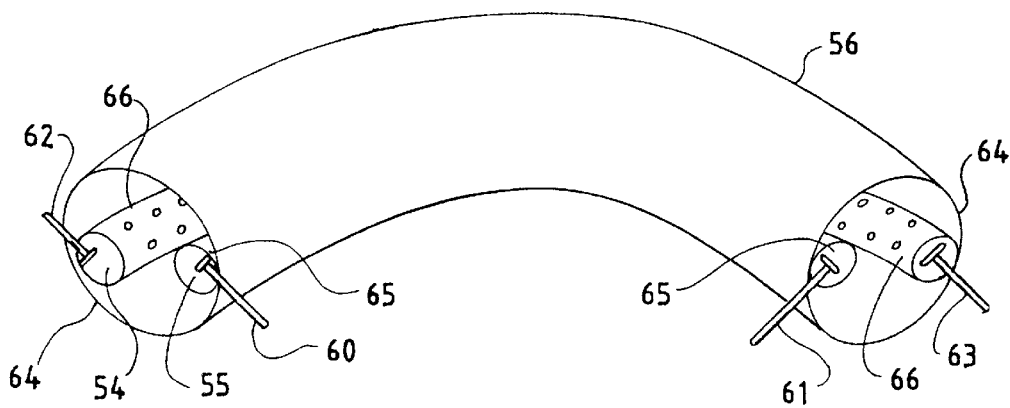
FIG. 10 illustrates an artificial heart valve utilizing an expandable copolymer gel under real time computer control.

FIG. 10 illustrates a heart valve using an expandable copolymer gel. The gel is contained in a pair of permeable membranes 55 and 56 that are formed into a toroidal shape; the membranes are contained within a toroidal-shape container 56. First membrane 55 is attached to the outer periphery of the container, while second membrane 56 is attached to the inner periphery of the container, as shown in FIG. 10. The container, in turn, is attached by stitches or other attachment means to the heart at the appropriate location. Periodic application of an electrical potential between first pair of electrode means 60, 61 and second pair of electrode means 62, 63 causes the toroid's outer surface 64 to expand while the inner surface 65 contracts, and vice versa. That opens and closes the valve. These functions can be controlled in real time by using computer-controlled voltages based on a pacemaker controlling the expansion and contraction of the heart muscles themselves, to coordinate opening and closing of the valves with expansion and contraction of the heart muscles.

It is known that response times for expansion and contraction of expandable copolymer gels are proportional to the linear dimensions of expandable copolymer gel elements, as noted in U.S. Pat. No. 5,100,933 (Tanaka, et al.). For large gel elements, response times can be undesirably slow. But, only comparatively simple shapes such as cylinders have been suggested for expandable copolymer gel devices.

I find that the slow response times of expandable copolymer gel elements result in large part from mass transfer limitations; swelling and contraction of the gel requires uptake and discharge of surrounding electrolyte solutions through the exterior boundary of the gel. Thus, by providing gel container shapes with extended surface areas, response times can be dramatically improved, by providing increased surface area for mass transfer. More specifically, instead of plain, cylindrical or flat gel shapes, the use of corrugations, perforations, fins and other extended surface areas is preferred. Thus, as shown in FIG. 9, a plurality of holes or perforations 66 may be employed to provide more-rapid response times for a sphincter-type heart valve.

Figure 11:
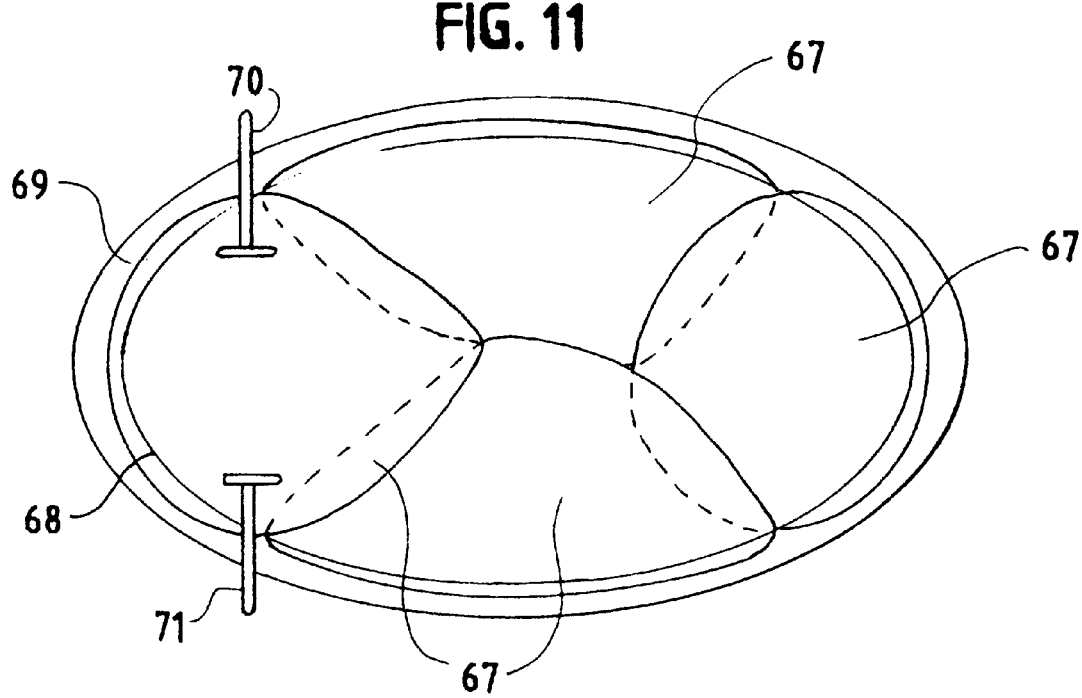
FIG. 11 illustrates an artificial heart valve utilizing an ER gel under real time computer control.

Another embodiment of a heart valve is shown in FIG. 11. This embodiment utilizes a plurality (preferably three to four) of flat, overlapping flaps 67 of roughly triangular shape, which are flexibly attached at one of their edges 68 to a toroidal base 69, which defines an interior aperture through which blood flows. The base 69 may be made of Core-Tex® or some other suitable material, and is designed to be sutured to the heart muscle. Each flap 67 contains an ER gel and is also fitted with electrode means 70, 71. The flap material is sufficiently flexible to allow it to freely bend in response to blood flow through the valve.

In response to the application of an electrical potential across electrode means 70 and 71, the ER gel contained in the flaps 67 becomes rigid. Response times for changes in properties of ER gels are very rapid; of the order of milliseconds. Thus, the flaps 67 of the heart valve of this embodiment can be "opened" and "closed" by alternately applying a voltage to hold the flaps rigidly against the base, and "opened" by removing the voltage to allow the flaps to become flexible and open in response to contraction of the chamber of the heart to which they are attached. As with the embodiment of FIG. 10, these functions can be controlled in real time by using computer-controlled voltages based on a pacemaker controlling the expansion and contraction of the heart muscles themselves, to coordinate opening and closing of the valves with expansion and contraction of the heart muscles.

It will be apparent to those of ordinary skill in the art that many changes and modifications could be made while remaining within the scope of my invention. I intend to cover all such equivalent processing methods, and to limit my invention only as specifically delineated in the following claims.

I claim:

1. A balloon catheter, comprising: an elongated tubular portion having a proximal end portion and a distal end portion; a balloon attached to said catheter near said distal end portion; at least one reservoir attached to said balloon; an expandable copolymer gel filling said reservoir; and first electrode means operably attached to said expandable copolymer gel enabling changes in the shape of said balloon in response to a voltage applied to said first electrode means.

2. The balloon catheter of claim 1, further comprising a flexible, elongated, hollow wall of said catheter; an ER gel filling said elongated hollow wall; and second electrode means operably connected to said ER gel, to enable said device to be made rigid or flexible in response to a voltage applied to said second electrode means.

* * * * *